United States Patent [19]

Sprecker et al.

[11] Patent Number: 4,668,432

[45] Date of Patent: May 26, 1987

[54] ALKYL-SUBSTITUTED-OXO-SPIRODECENENE DERIVATIVES, ORGANOLEPTIC UTILITY THEREOF AND PROCESSES FOR PREPARING SAME

[75] Inventors: Mark A. Sprecker, Sea Bright; Marie R. Hanna, Hazlet, both of N.J.

[73] Assignee: International Flavors & Fragrances Inc., New York, N.Y.

[21] Appl. No.: 879,425

[22] Filed: Jun. 27, 1986

[51] Int. Cl.[4] .......... A61K 7/46

[52] U.S. Cl. .......... 252/522 R; 560/231; 568/367; 568/816

[58] Field of Search .......... 252/522 R; 568/347, 568/367, 816; 560/231

[56] References Cited

U.S. PATENT DOCUMENTS

| | | | |
|---|---|---|---|
| 4,052,457 | 10/1977 | Nogakura et al. | 568/367 |
| 4,261,866 | 4/1981 | Barton et al. | 568/367 |
| 4,430,508 | 2/1984 | Sprecker et al. | 252/522 R |

OTHER PUBLICATIONS

Nerdel et al, Ann. Chem., vol. 710, pp. 90–97 (1967).

Tanaka et al, J. Chem. Soc., Chem. Comm., pp. 188–189 (1967).

Sobaleva et al, Chem. Abst, vol. 80, #145536r (1975).

*Primary Examiner*—James H. Reamer

*Attorney, Agent, or Firm*—Arthur L. Liberman

[57] ABSTRACT

Described are alkyl-substituted-oxo-spirodecenene derivatives defined according to the structure:

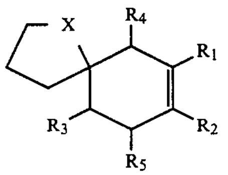

wherein X represents carbinol, carbinol $C_1$–$C_3$ alkanoate or ketone; one of $R_1$, $R_2$, $R_4$ and $R_5$ represents methyl and the other of $R_1$, $R_2$, $R_4$ and $R_5$ represents hydrogen; and $R_3$ is n-butyl or isopropyl and uses thereof in augmenting or enhancing the aroma of perfume compositions, colognes and perfumed articles including but not limited to solid or liquid anionic, cationic, nonionic or zwitterionic detergents, fabric softener compositions, fabric softener articles and hair preparations; as well as processes for preparing said alkyl-substituted-oxo-spirodecenene derivatives.

12 Claims, 11 Drawing Figures

GLC PROFILE FOR EXAMPLE I(A).
CRUDE

NMR SPECTRUM FOR EXAMPLE I(A), PEAK 10 OF FIG.1.

GLC PROFILE FOR EXAMPLE I(B). CRUDE

GLC PROFILE FOR EXAMPLE II.
CRUDE

NMR SPECTRUM FOR EXAMPLE II

GLC PROFILE FOR EXAMPLE III. CRUDE

NMR SPECTRUM FOR EXAMPLE III.

GLC PROFILE FOR EXAMPLE IV.
CRUDE

NMR SPECTRUM FOR FRACTION 9 OF EXAMPLE IV.

ALKYL-SUBSTITUTED-OXO-SPIRODECENENE DERIVATIVES, ORGANOLEPTIC UTILITY THEREOF AND PROCESSES FOR PREPARING SAME

BACKGROUND OF THE INVENTION

The instant invention relates to alkyl-substituted-oxo-spirodecenene derivatives defined according to the structure:

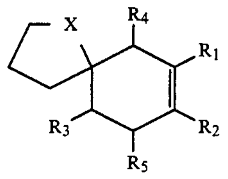

wherein X represents carbinol, carbinol $C_1$–$C_3$ alkanoate or ketone; wherein one of $R_1$, $R_2$, $R_4$ and $R_5$ represents methyl and the other of $R_1$, $R_2$, $R_4$ and $R_5$ each represent hydrogen; and $R_3$ represents n-butyl or isopropyl and uses of same in augmenting or enhancing the aroma of perfume compositions, perfumed articles and colognes.

Inexpensive chemical compounds which can provide cardamon, figgy, date-like, vetiver, floral, rose, woody, musky, incense-like, olibanum, spicy, camphoraceous, natural balsamic and lemony aromas with spicy, minty, fruity, rose, sweaty, animalic, sweet, musky, floral, jasmine and fatty topnotes are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Spiro ketones are known in the prior art and their utilities in many instances are known in perfumery.

Thus, Japanese Published Application 76/65738 (abstracted at Chemical Abstracts 85:123440f) (corresponding to U.S. Pat. No. 4,052,457 issued on Oct. 4, 1977) discloses the compound having the structure:

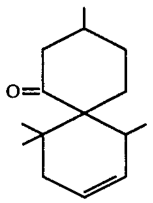

as being useful in perfumery and further discloses the process according to the reaction:

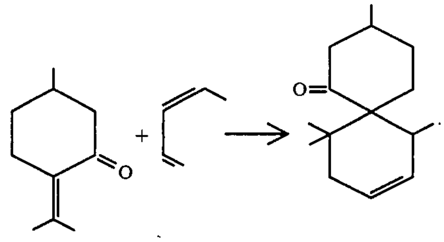

Nerdel and Dahl, *Ann. Chim.*, 710, 90 (1967) discloses the compound having the structure:

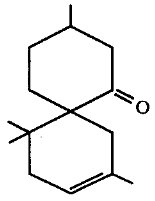

and the generic process, to wit:

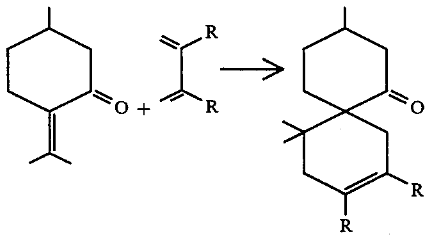

(wherein R represents hydrogen or methyl).

Tanaka, et al, Chem.Comm. 1967, page 188 (title of paper: "The Total Synthesis of Chamigrene" discloses the compound having the structure:

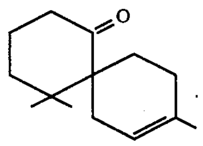

U.S. Pat. No. 4,261,866 issued on Apr. 14, 1981 (Class 252, Subclass 522R) discloses the genus of compounds having the structure:

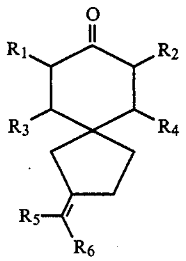

wherein $R_1$–$R_6$ each represents hydrogen or lower alkyl. U.S. Pat. No. 4,261,866 further discloses the broad genus, to wit:

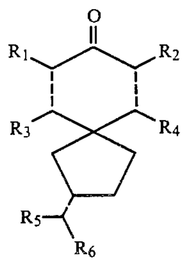

wherein each of the dashed lines represent carbon-carbon single bonds and carbon-carbon double bonds. The compounds disclosed in U.S. Pat. No. 4,261,866 are indicated to be useful in perfumery.

However, the alkyl-substituted-oxo-spirodecenene derivatives of our invention have unexpected, unobvious and advantageous perfumery properties when compared with the perfumery properties of the above-cited prior art.

In addition, copending application for United States Letters Patent, Ser. No. 805,739 filed on Dec. 6, 1985 assigned to the assignee of the instant application, International Flavors & Fragrances Inc., relates to alkyl-substituted spiro undecenone derivatives defined according to the structure:

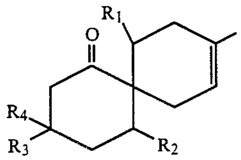

wherein $R_1$ represents isopropyl or hydrogen and $R_2$, $R_3$ and $R_4$ are each the same and each represents methyl or hydrogen; with the provisos:

(i) that when $R_1$ is isopropyl, $R_2$, $R_3$ and $R_4$ are hydrogen; and (ii) when $R_2$, $R_3$ and $R_4$ are methyl, $R_1$ is hydrogen, and uses of same in augmenting or enhancing the aroma of perfume compositions, perfumed articles and colognes.

The structures of the compounds of application for U.S. Letters Patent, Ser. No. 805,739 filed on Dec. 6, 1985 are different in kind rather than degree from the structures of the alkyl-substituted-oxo-spirodecenene derivatives of our invention.

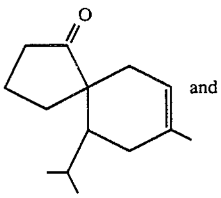

and

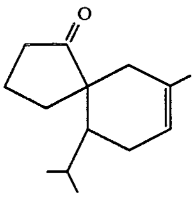

(Conditions: SE-30 column programmed at 180° C. isothermal).

Figure 1:
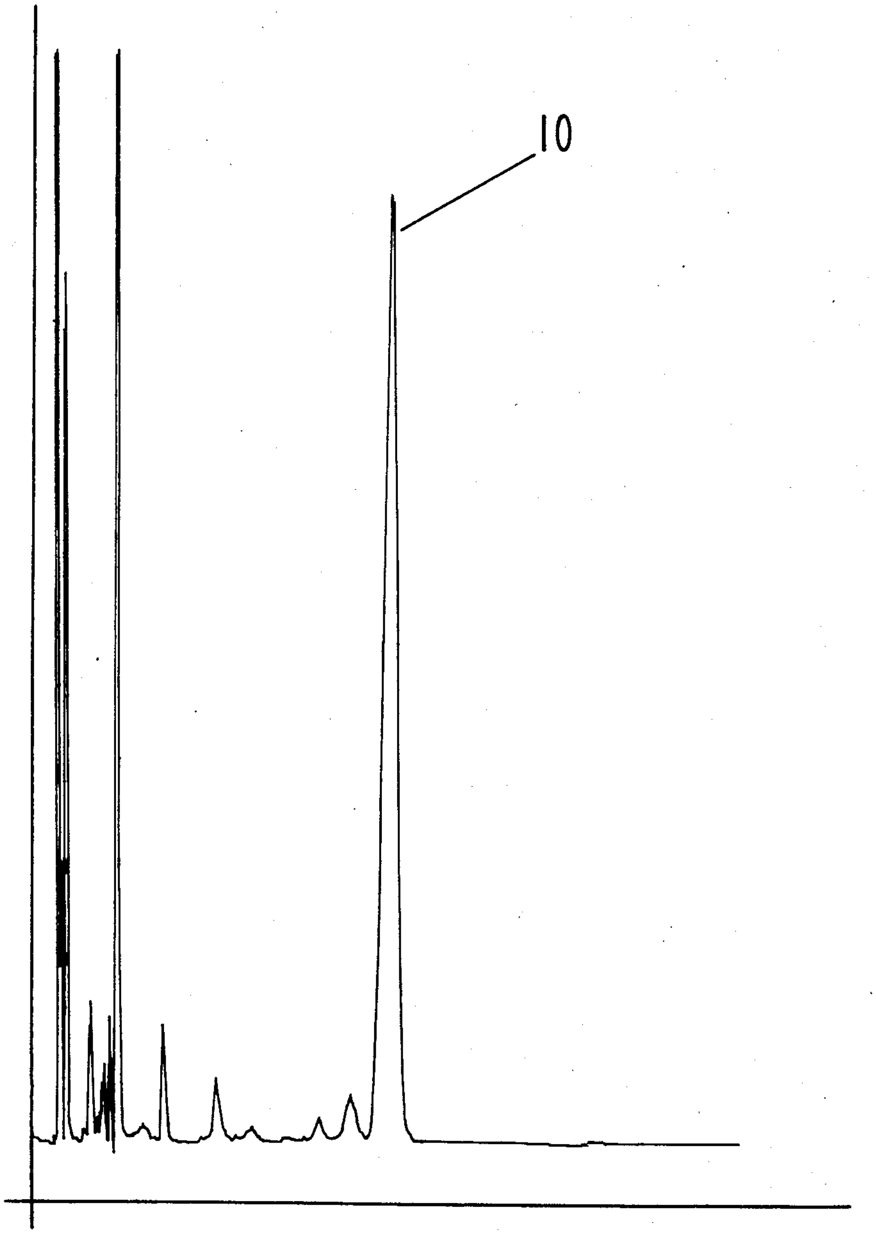
FIG. 1 is the GLC profile for the crude reaction product of Example I(A) containing the mixture of compounds having the structures.
Figure 2:
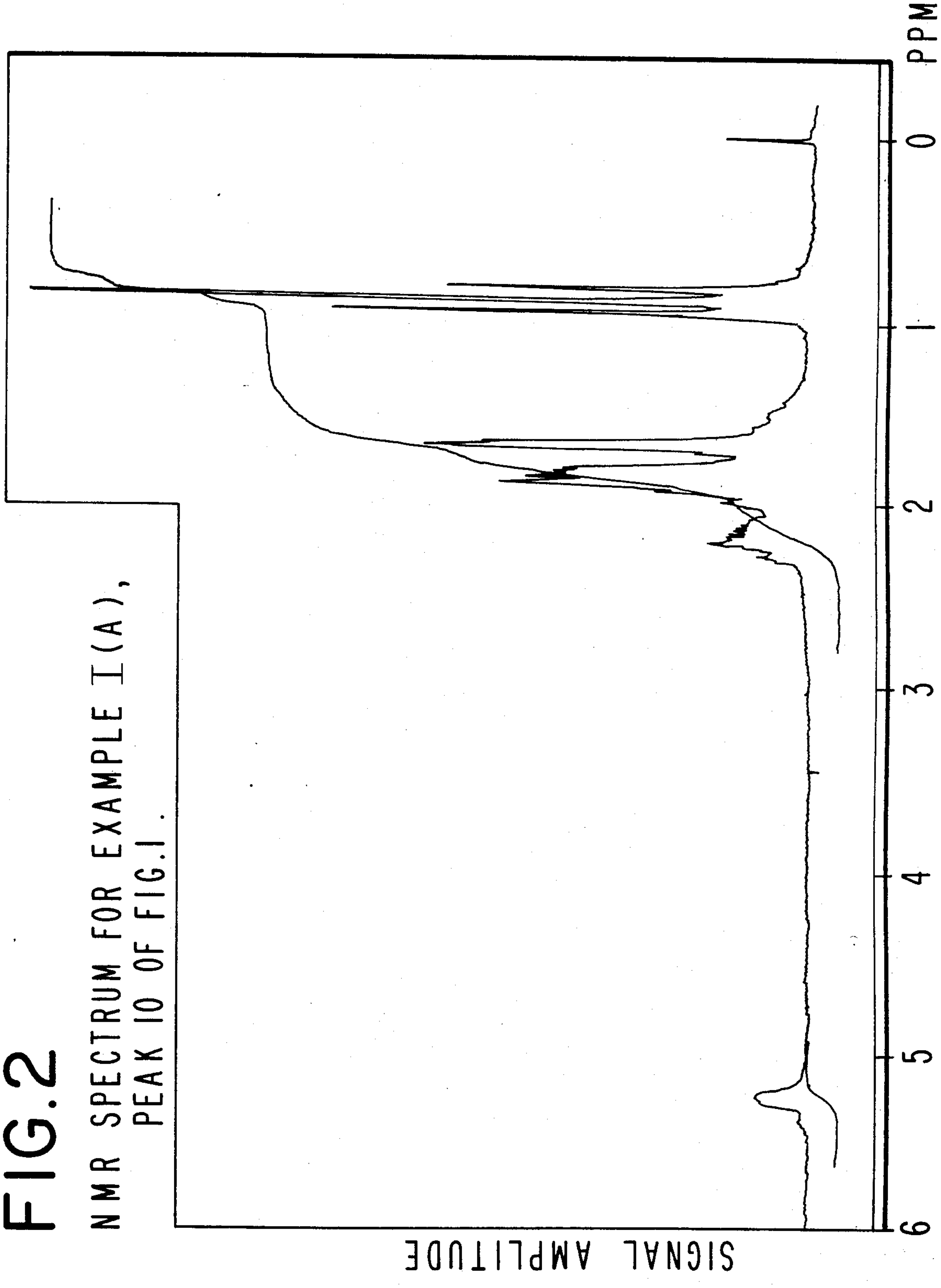

FIG. 2 is the NMR spectrum for the peak indicated by reference numeral 10 on the GLC profile of FIG. 1 for the mixture of compounds having the structures:

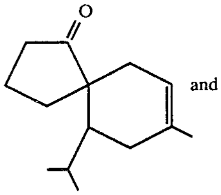

and

Figure 3:
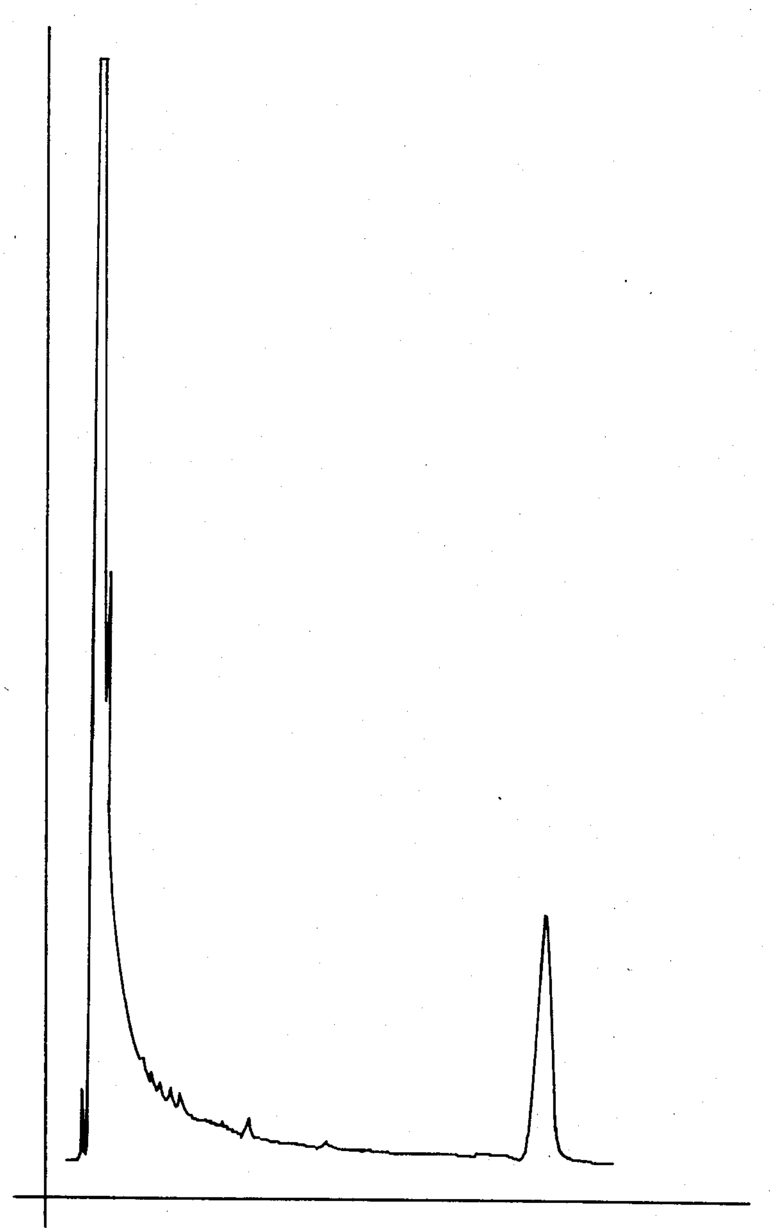

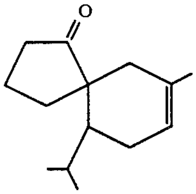

produced according to Example I(A):

FIG. 3 is the GLC profile for the crude reaction product of Example I(B) containing the compounds having the structures:

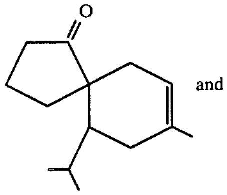

and

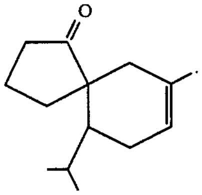

Figure 4:
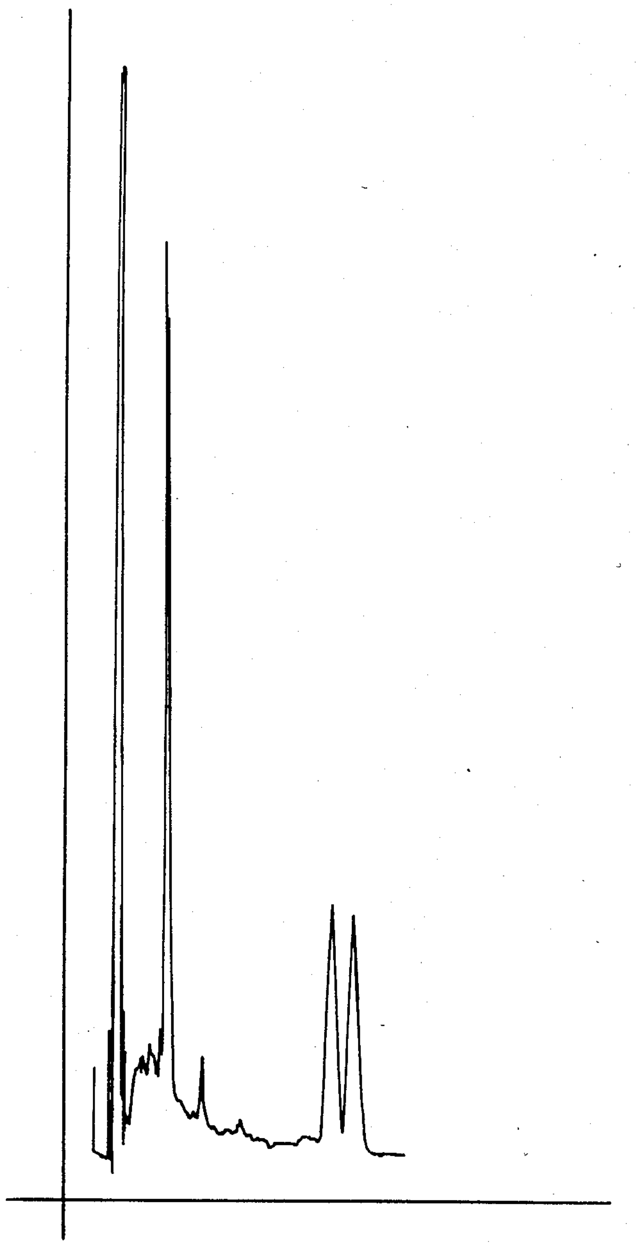

FIG. 4 is the GLC profile for the crude reaction product of Example II containing the compounds having the structures:

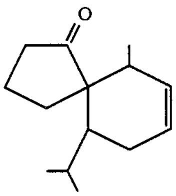

and

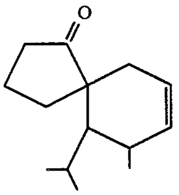

in admixture.

Figure 5:
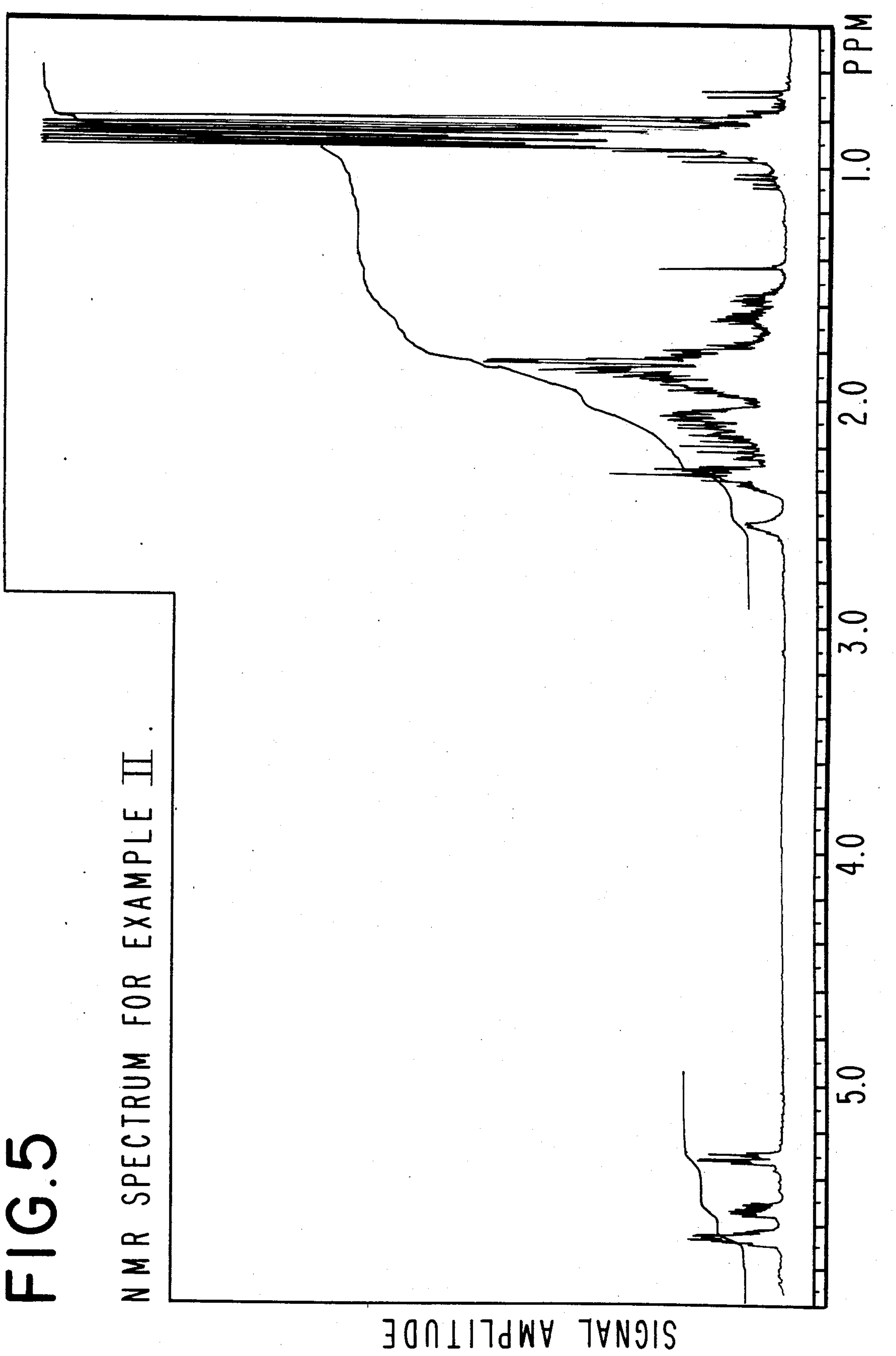

FIG. 5 is the NMR spectrum for the mixture of compounds having the structures:

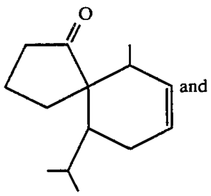

and

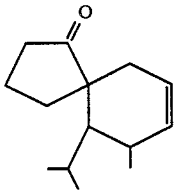

produced according to Example II.

Figure 6:
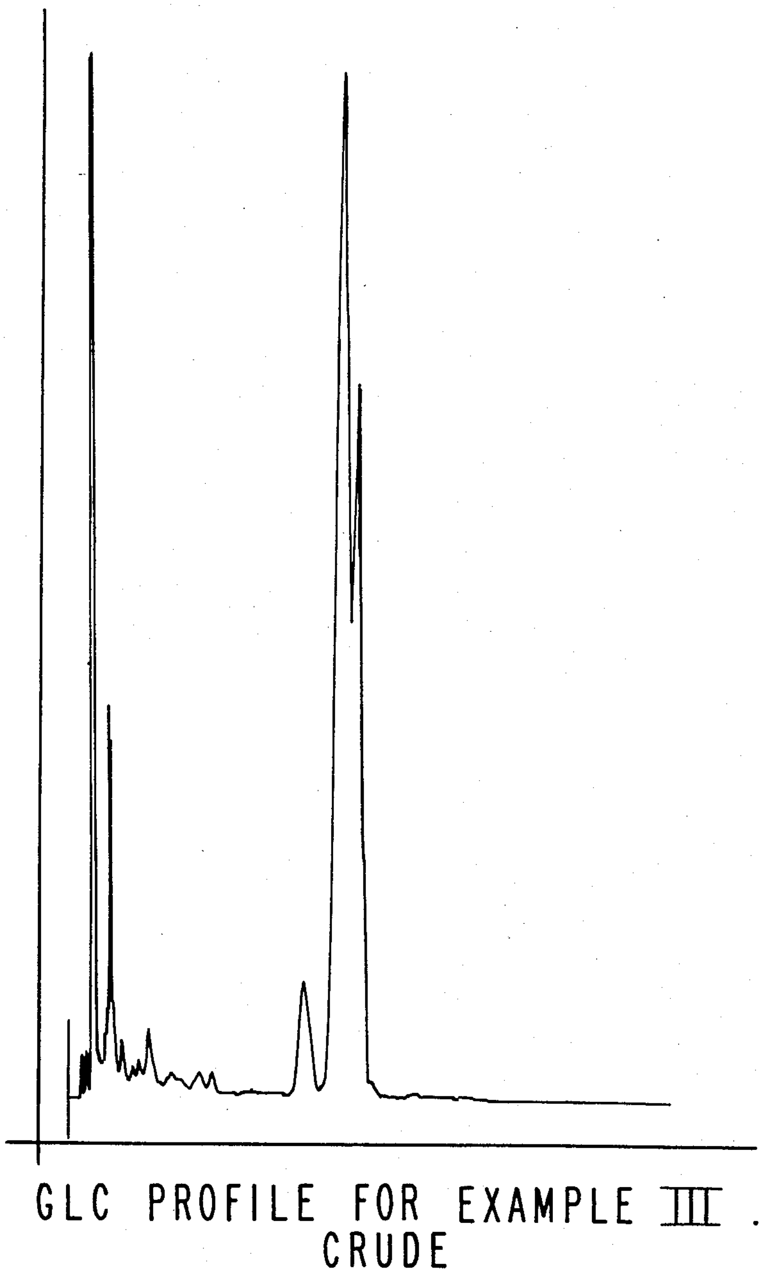

FIG. 6 is the GLC profile for the crude reaction product of Example III containing the compounds having the structures:

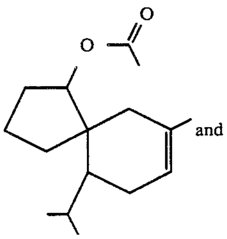

and

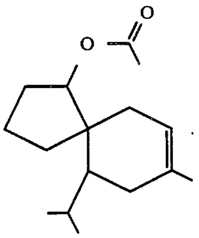

Figure 7:
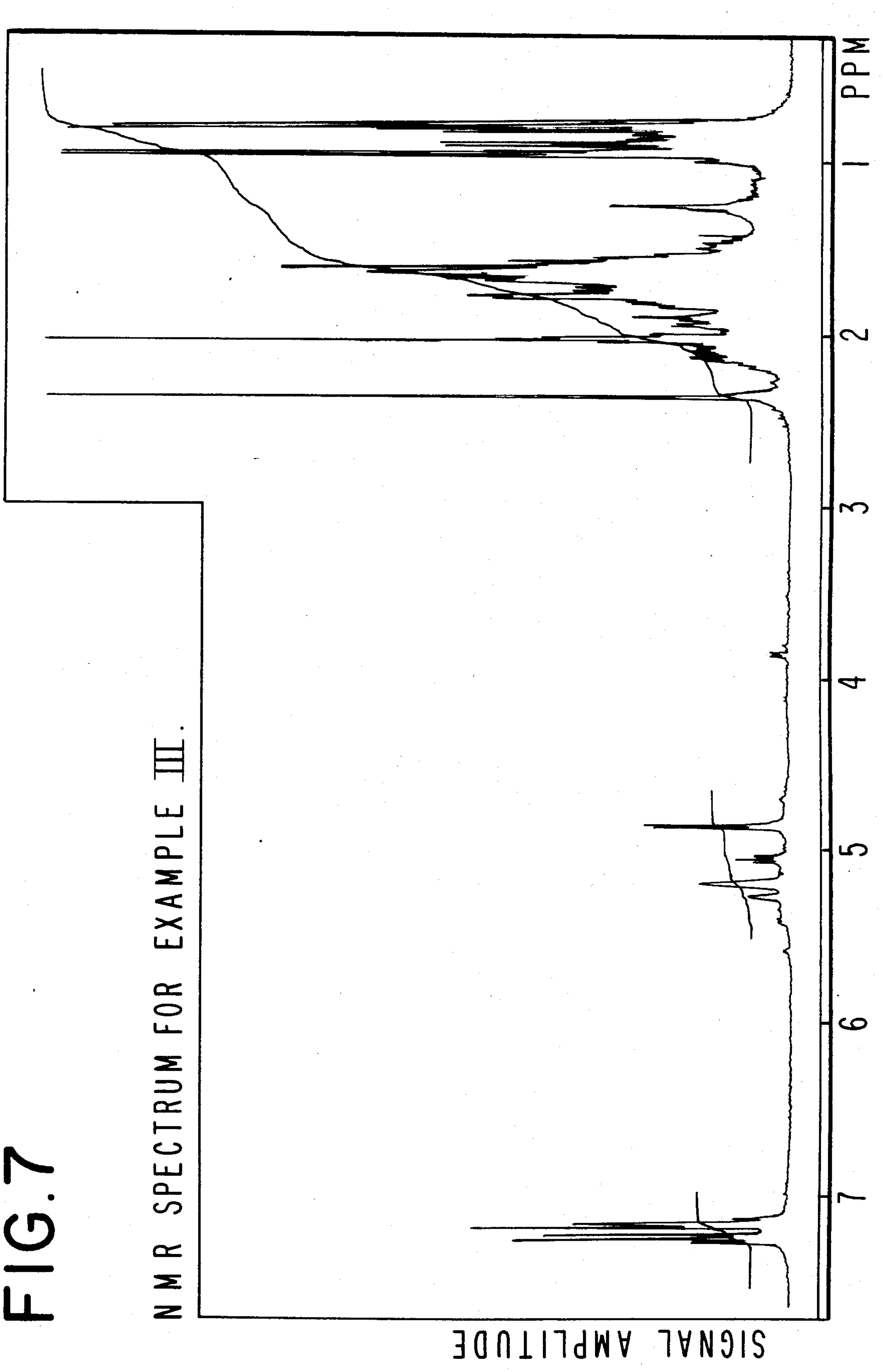

FIG. 7 is the NMR spectrum for the mixture of compounds having the structures:

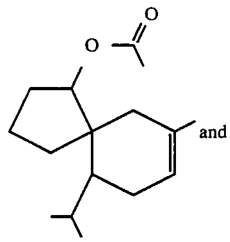 and 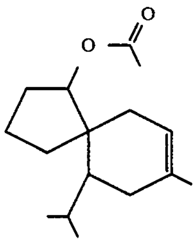

prepared according to Example III.

Figure 8:
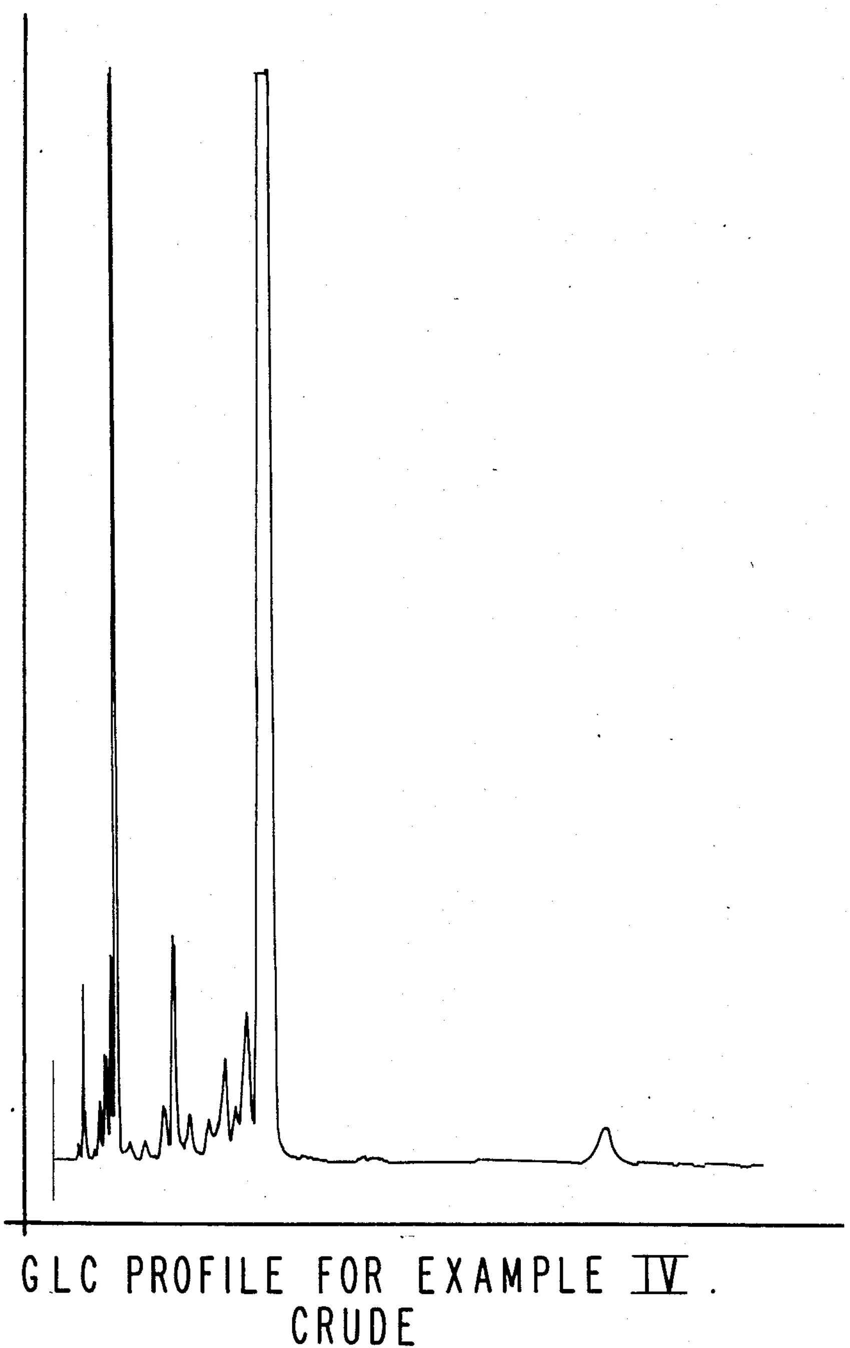

FIG. 8 is the GLC profile for the crude reaction product prepared according to Example IV containing the compounds having the structures:

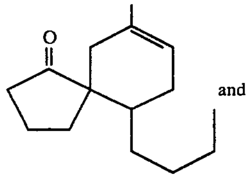 and 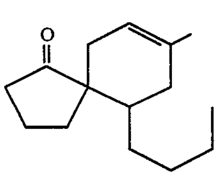

(Conditions: SE-30 column programmed at 180° C. isothermal).

Figure 9:
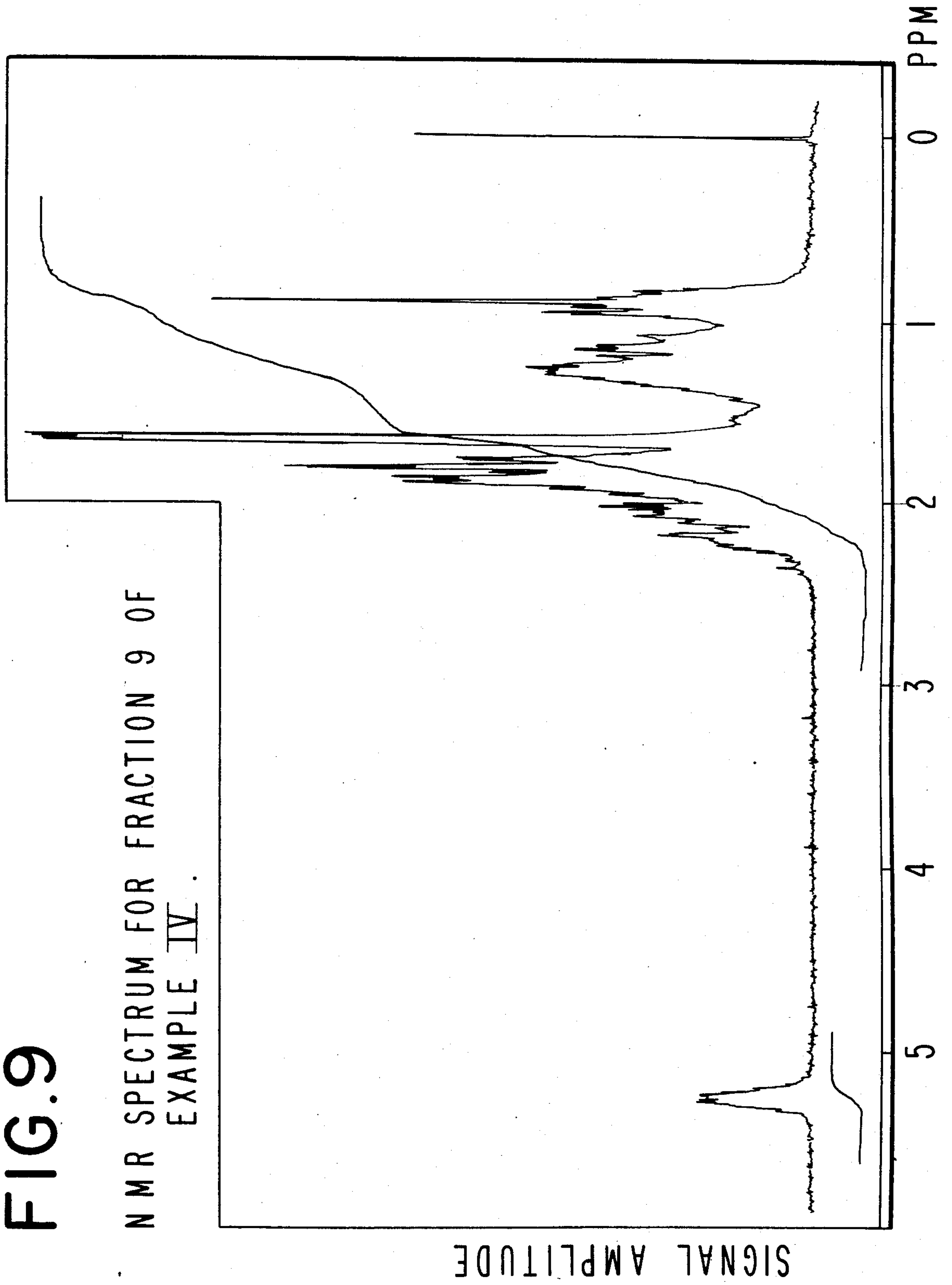

FIG. 9 is the NMR spectrum for Fraction 9 of the distillation product of the reaction product of Example IV containing the compounds having the structures:

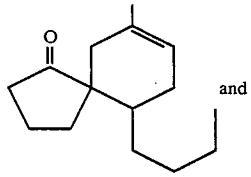 and 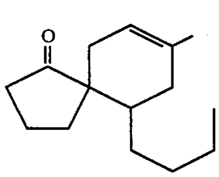

(Conditions: Field strength: 100 MHz; Solvent: $CFCl_3$).

Figure 10:
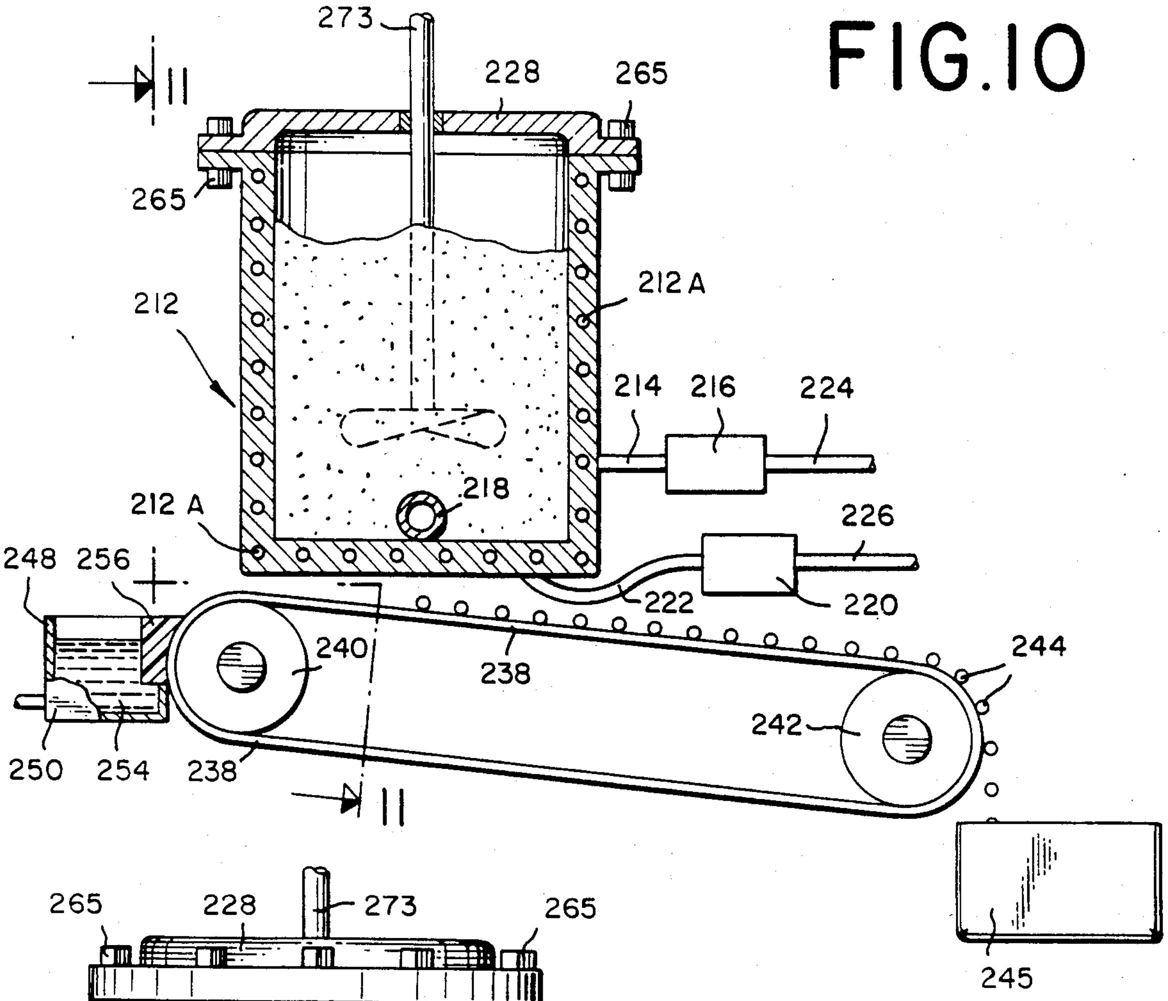

FIG. 10 is a partial side elevation and partial sectional view of an apparatus for forming polymer pellets containing at least one of the alkyl-substituted-oxo-spirodecenene derivatives of our invention.

Figure 11:
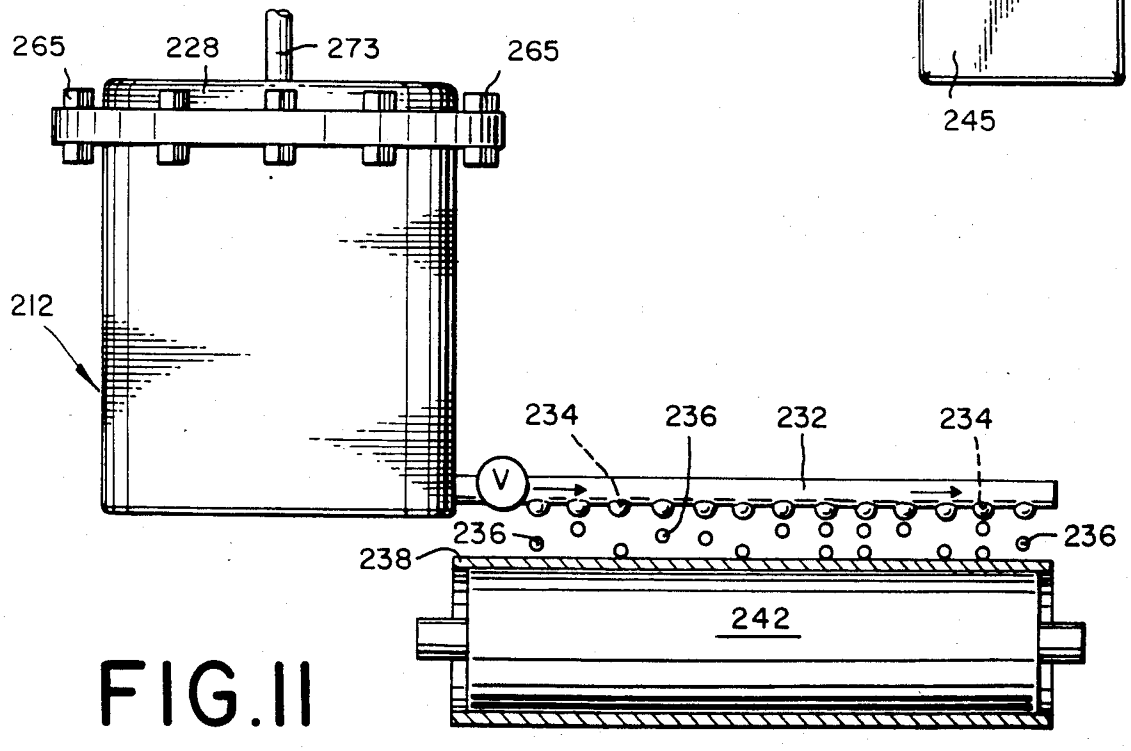

FIG. 11 is a section taken along the line 11—11 of FIG. 10.

DETAILED DESCRIPTION OF THE DRAWINGS

FIG. 1 is the GLC profile for the crude reaction product of Example I(A) containing the compounds having the structures:

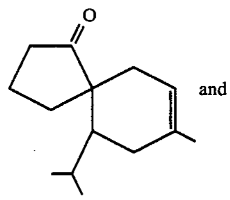 and 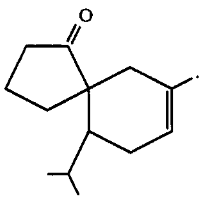

The peak indicated by reference numeral 10 is the peak for the product containing the mixture of compounds having the structures:

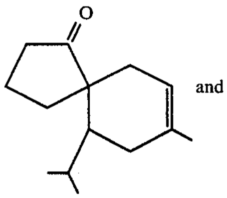 and 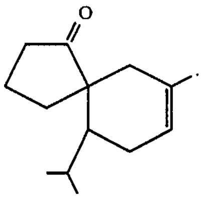

Referring to FIGS. 10 and 11, the apparatus used in producing polymeric fragrances containing the alkyl-substituted-oxo-spirodecenene derivatives of our invention comprises a device for forming scented polyolefin (for example) pellets, which comprises a vat or container 212 into which a mixture of polyolefin such as polyethylene and an aromatic substance or scented material is placed (in this case at least one of the alkyl-substituted-oxo-spirodecenene derivatives of our invention). The container is closed by an air-tight lid 228 and clamped to the container by bolts 265. A stirrer 273 traverses the lid or cover 228 in air-tight manner and is rotated in a suitable manner.

A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with viscosity ranging between 180 and 220 saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through a control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the alkyl-substituted-oxo-spirodecenene derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the alkyl-substituted-oxo-spirodecenene derivatives of our invention) are added to the polyolefin.

After the scent imparting material (e.g., a composition containing at least one of the alkyl-substituted-oxo-spiro-decenene derivatives of our invention) is added to the container 212, the mixture is stirred for a few minutes, for example, 5–15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A or heating purposes.

Thereafter the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., at least one of the alkyl-substituted-oxo-spirodecenene derivatives of our invention) will continuously drop through orifices 234 downwardly from conduit 232. During this time the temperature of the polymer (e.g., polyolefin) and scent imparting material (e.g., a mixture containing at least one of the alkyl-substituted-oxo-spirodecenene derivatives of our invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the alkyl-substituted-oxo-spirodecenene derivatives of our invention) mixture through the orifices 234 at a rate which will insure the formation of droplets 236 which will fall downwardly onto a moving conveyor belt 238 caused to run between the conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

THE INVENTION

The present invention provides alkyl-substituted-oxospirodecenene derivatives defined according to the structure:

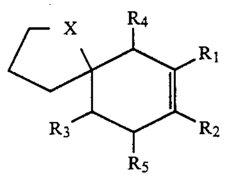

wherein X represents carbinol, carbinol $C_1$-$C_3$ alkanoate or ketone; one of $R_1$, $R_2$, $R_4$ and $R_5$ represents methyl and the other of $R_1$, $R_2$, $R_4$ and $R_5$ each represents hydrogen; and $R_3$ represents n-butyl or isopropyl.

The compositions of matter of our invention produced according to the processes of our invention are capable of augmenting, enhancing or providing cardamon, figgy, date-like, vetiver, floral, rose, woody, musky, incense-like, olibanum, spicy, camphoraceous, natural balsamic and lemony aromas with spicy, minty, fruity, rose, sweaty, animalic, sweet, musky, floral, jasmine and fatty topnotes to perfume compositions, colognes and perfumed articles, (e.g., solid or liquid anionic, cationic, nonionic or zwitterionic detergents, fabric softener articles, drier-added fabric softener articles, fabric softener compositions, cosmetic powders, hair preparations and perfumed polymers and the like).

The alkyl-substituted-oxo-spirodecenene derivatives of our invention are first prepared by reacting cyclopentenone with isobutyraldehyde or n-pentanal via an "aldol" condensation reaction, first forming the compound having the structure:

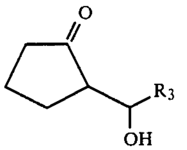

and then by means of dehydrating same forming the compound having the structure:

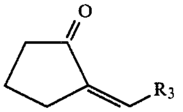

according to the reaction:

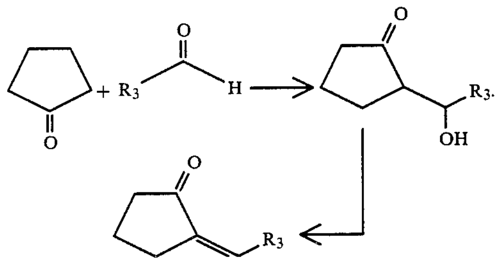

The compound having the structure:

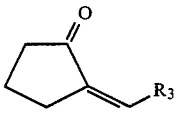

is then reacted with isoprene or 1,3-pentadiene which compounds fall within the genus having the structure:

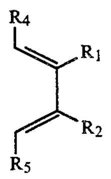

wherein one of $R_1$, $R_2$, $R_4$ and $R_5$ is methyl and the other of $R_1$, $R_2$, $R_4$ and $R_5$ is hydrogen and wherein $R_3$ is isopropyl or n-butyl, in order to form a compound which is a member of the genus having the structure:

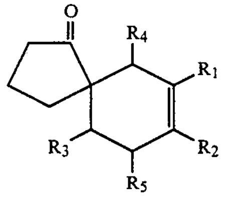

according to the reaction:

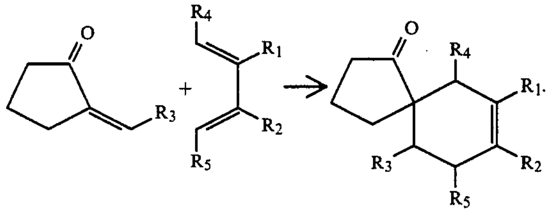

The reaction:

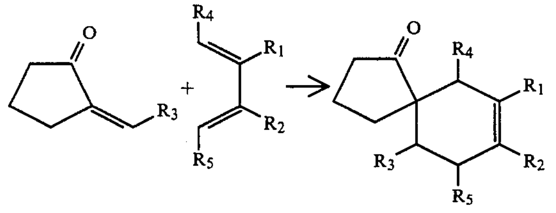

takes place in the presence of a Lewis acid catalyst such as aluminum trichloride and in the presence of an inert solvent, e.g., methylene dichloride or toluene at a temperature in the range of from about 20° C. up to about 50° C. (preferably about 35°–45° C.). The mole ratio of the compound having the structure:

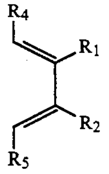

to the compound having the structure:

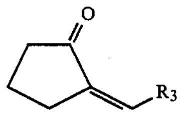

is about 1:1 with an excess of the compound having the structure:

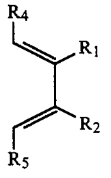

being present. The amount of Lewis acid (e.g., aluminum chloride) in the reaction mass is in an amount about equimolar to the compound having the structure:

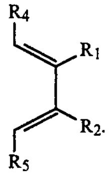

It is preferred that the compound having the structure:

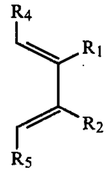

be in slight excess in the reaction mass, e.g., from about 3 up to about 10% in excess. The amount of inert solvent in the reaction mass, e.g., methylene dichloride or toluene may vary from about 40% up to about 150% of the reaction mass.

At the end of the reaction, the reaction mass may be washed (e.g., with sodium chloride solution) until neutral and then fractionally distilled to yield odor acceptable material or to yield material which may be further reacted as by reduction and subsequent (optionally) esterification.

Accordingly, the ketone which is a member of the genus having the structure:

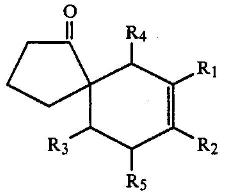

may be reduced, for example, using a reducing agent such as sodium borohydride or aluminum triisopropylate whereby the ring double bond is not affected but the ketone is reduced to hydroxyl according to the reaction:

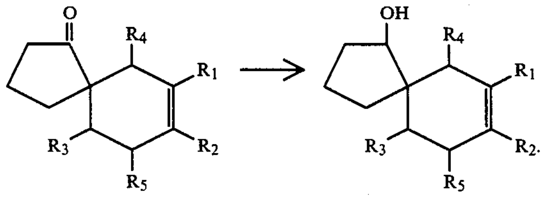

The mole ratio of the compound having the structure:

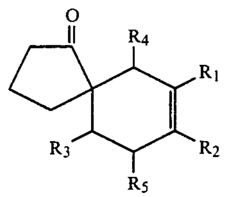

to reducing agent, (e.g., lithium aluminum hydride, sodium borohydride or aluminum triisopropylate) may vary from about 0.2:1 up to about 1:1. The reaction is carried out in the presence of an inert solvent such as methyl alcohol or ethyl alcohol. The concentration of the ketone having the structure:

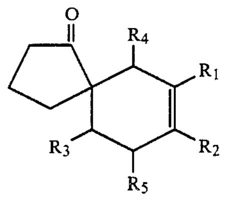

in the reaction mass may vary from about 15% up to about 60%. The reaction is preferably carried out under reflux conditions, e.g., from about 70° C. up to about 100° C. depending upon the pressure over the reaction mass which may vary from about 0.9 atmospheres up to about 10 atmospheres, preferably about 1 atmosphere. The time of reaction may vary from about 5 hours up to about 15 hours depending on the temperature of reaction and the desired yield.

At the end of the reaction, the reaction mass is quenched with aqueous acid, e.g., aqueous concentrated hydrochloric acid and then rinsed with water. The reaction product is then distilled via fractional distillation to yield a compound which is a member of the genus having the structure:

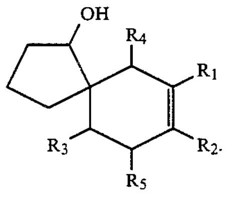

This compound can be used as is for its organoleptic properties or may be further reacted as with an alkanoic acid anhydride having the structure:

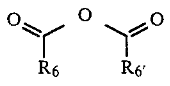

wherein $R_6$ and $R_{6'}$ are the same or different $C_1$–$C_3$ alkyl to yield the compound having the structure:

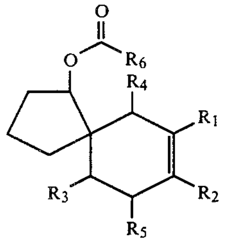

according to the reaction:

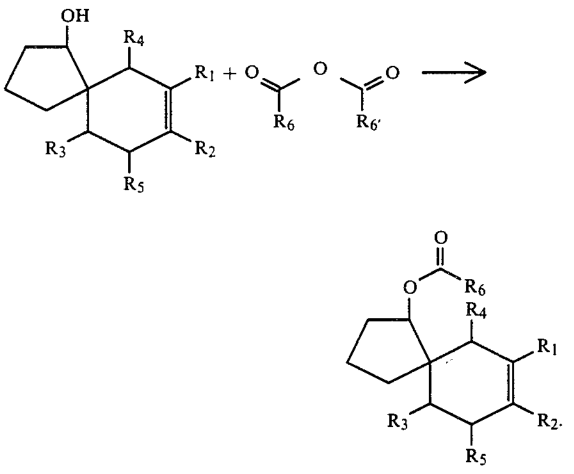

The esterification reaction is carried out under standard esterification conditions, e.g., reflux conditions for a period of time of between about 0.5 hours and 5 hours. The mole ratio of the compound having the structure:

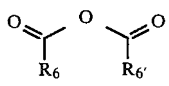

to the compound having the structure

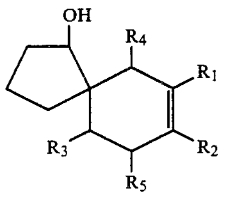

is between about 1:1 and about 2:1. Furthermore, the temperature of reaction may vary between about 120° C. and 150° C. depending upon the particular compound having the structure:

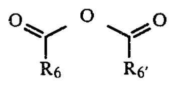

used and the particular compound having the structure:

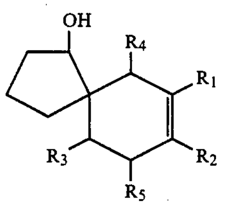

used and the pressure over the reaction mass, e.g., from about 0.9 atmospheres up to about 5 atmospheres.

At the end of the reaction, the reaction mass is cooled (e.g., to between about 60° and about 80° C.) and water is added to quench the reaction mass. The reaction mass is then washed with water and the organic phase is separated from the aqueous phase. The organic phase is washed with weak base, e.g., 5% sodium bicarbonate solution) and then distilled using fractional distillation to yield the product having the structure:

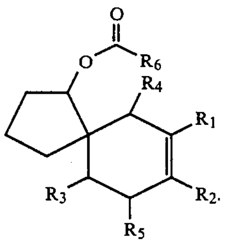

Examples of the alkyl-substituted-oxo-spirodecenene derivatives of our invention are set forth in the following Table I:

TABLE I

| Alkyl-Substituted-Oxo-Spirodecenene Derivatives of Our Invention | Perfumery Properties |
|---|---|
| A mixture of compounds having the structures: 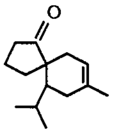 and 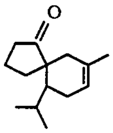 prepared according to Example I(A), bulked distillation Fractions 7-12. | A cardamon, figgy, date-like, vetiver, floral, rose and woody aroma with spicy, minty, fruity and rose topnotes. |

TABLE I-continued

| Alkyl-Substituted-Oxo-Spirodecenene Derivatives of Our Invention | Perfumery Properties |
|---|---|
| A mixture of compounds having the structures: 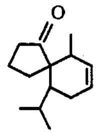 and 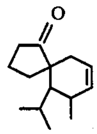 prepared according to Example II, bulked distillation Fractions 3-7. | A rosy, woody and musky aroma with minty topnotes. |
| A mixture of compounds having the structures: 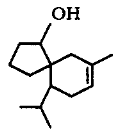 and 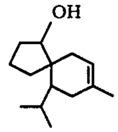 prepared according to Example III(A), bulked distillation Fractions 3-13. | A woody aroma with sweaty and animalic topnotes. |
| A mixture of compounds having the structures: 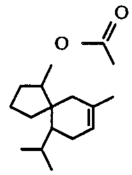 and 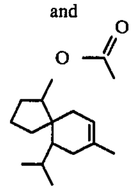 prepared according to Example III(B), bulked distillation Fractions 5-9. | An incense-like, olibanum aroma with sweet, woody, musky and animalic topnotes. |

TABLE I-continued

| Alkyl-Substituted-Oxo-Spirodecenene Derivatives of Our Invention | Perfumery Properties |
|---|---|
| A mixture of compounds having the structures: 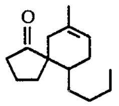 and 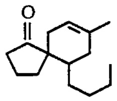 prepared according to Example IV, bulked distillation Fractions 7-13. | A woody, spicy, camphorceous, natural balsamic and lemony aroma with woody, floral, jasmine, minty and fatty topnotes. |

One or more of the alkyl-substituted-oxo-spirodecenene derivatives prepared in accordance with the processes of our invention and one or more auxiliary perfume ingredients including, for example, alcohol other than the alkyl-substituted-oxo-spirodecenene derivatives of our invention; aldehydes, ketones other than the alkyl-substituted-oxo-spirodecenene derivatives of our invention, terpenic hydrocarbons, nitriles, esters other than the alkyl-substituted-oxo-spirodecenene derivatives of our invention, lactones, natural essential oils and synthetic essential oils may be admixed so that the combined odors of the individual components produce a pleasant and desired fragrance, particularly and preferably in the woody, minty, herbaceous, musky and spicy fragrances. Such compositions usually contain:

(a) the main note or the "bouquet" or foundation stone of the composition;
(b) modifiers which round-off and accompany the main note:
(c) fixatives which include odorous substances which lend a particular note to the perfume throughout all stages of evaporation and substances which retard evaporation; and
(d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the alkyl-substituted-oxo-spirodecenene derivatives prepared in accordance with the process of our invention can be used to alter, modify or enhance the aroma characteristics of a perfume composition, for example, by utilizing or moderating the olfactory reaction contributed by another ingredient in the composition.

The amount of the alkyl-substituted-oxo-spirodecenene derivatives prepared in accordance with the processes of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the alkyl-substituted-oxo-spirodecenene derivatives prepared in accordance with the processes of our invention or even less (e.g., 0.005%) can be used to impart, augment or enhance cardamon, figgy, date-like, vetiver, floral, rose, woody, musky, incense-like, olibanum, spicy, camphoraceous and natural balsamic and lemony aroma with spicy, minty, fruity, rose, sweaty, animalic, sweet, musky, floral, jasmine and fatty topnotes to soaps, cosmetics, anionic, cationic, nonionic or zwitterionic detergents, fabric softener compositions, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The alkyl-substituted-oxo-spirodecenene derivatives prepared in accordance with the processes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders, such as talcs, dusting powders, face powders, microporous "perfumed" slow release polymers and the like.

When used as (an) olfactory component(s) in perfumed articles, as little as 0.005% of the alkyl-substituted-oxo-spirodecenene derivatives prepared in accordance with the processes of our invention will suffice to impart, augment or enhance cardamon, figgy, date-like, vetiver, floral, rose, woody, musky, incense-like, olibanum, spicy, camphoraceous and natural balsamic and lemony aroma with spicy, minty, fruity, rose, sweaty, animalic, sweet, musky, floral, jasmine and fatty topnotes. Generally, no more than 6% of the alkyl-substituted-oxo-spirodecenene derivatives of our invention based on the ultimate end product is required in the perfumed article. Accordingly, the range of use of the alkyl-substituted-oxo-spirodecenene derivatives of our invention in perfumed articles, per se, is from about 0.005% up to about 6% by weight based on the perfumed article.

In addition, the perfume composition or fragrance composition of our invention can contain a vehicle or carrier for the alkyl-substituted-oxo-spirodecenene derivatives prepared in accordance with the processes of our invention. The vehicle can be a liquid such as a non-toxic alcohol, e.g., ethyl alcohol, a non-toxic glycol, e.g., propylene glycol or the like. The carrier can be an absorbent solid such as a gum (e.g., gum arabic, guar gum or xanthan gum or combination thereof) or components for encapsulating the composition (such as gelatin as by coacervation) or using prepolymers such as urea-formaldehyde prepolymers which are able to form a urea-formaldehyde polymer capsule around a liquid perfume center.

It will thus be apparent that the alkyl-substituted-oxo-spirodecenene derivatives prepared in accordance with the processes of our invention can be utilized to alter, modify or enhance sensory properties particularly organoleptic properties such as fragrances of a wide variety of consumable materials.

The following Examples I-IV set forth means for preparing the alkyl-substituted-oxo-spirodecenene derivatives of our invention. The examples including and following Example V set forth illustrations of organoleptic utilities of the alkyl-substituted-oxo-spirodecenene derivatives of our invention.

All parts and percentages given herein are by weight unless otherwise specified.

EXAMPLE I(A)

PREPARATION OF MIXTURE OF 7 AND 8-METHYL-10-ISOPROPYL-SPIRO[4.5]DEC-7-EN1-ONE

Reaction:

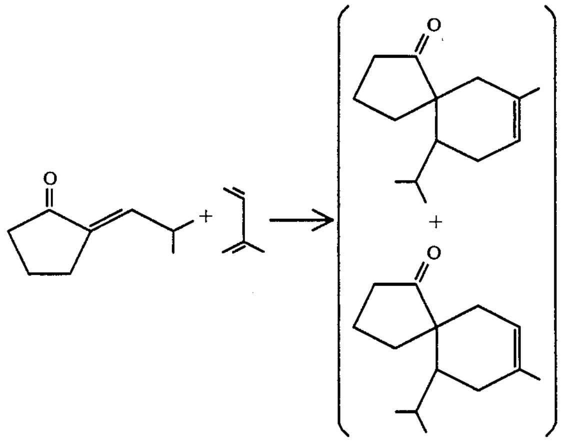

Into a 2 liter reaction vessel equipped with stirrer, thermometer, reflux condenser and cooling bath are placed 500 ml methylene dichloride and 6.75 moles of aluminum trichloride (anhydrous). With stirring, 610 grams (5 moles) of isobutylidene cyclopentenone are added over a period of 15 minutes with cooling, maintaining the reaction mass at 20° C. Over a three hour period, while maintaining the reaction mass at 25° C. with stirring, 476 grams (7 moles) of isoprene are added to the reaction mass. The reaction mass is then heated with stirring to 40° C. and maintained at 40° C. for a period of four hours with stirring.

The reaction mass is then washed with 1 liter of saturated sodium chloride solution followed by 1 liter of 10% sodium carbonate solution.

The reaction mass is then distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 65/ | 120/ | 3.0 |
| 2 | 65 | 120 | 3.0 |
| 3 | 106 | 125 | 3.0 |
| 4 | 109 | 127 | 3.0 |
| 5 | 108 | 123 | 3.0 |
| 6 | 110 | 126 | 2.5 |
| 7 | 110 | 125 | 2.5 |
| 8 | 110 | 125 | 2.5 |
| 9 | 110 | 125 | 2.5 |
| 10 | 110 | 125 | 2.5 |
| 11 | 109 | 125 | 2.5 |
| 12 | 109 | 125 | 2.5 |
| 13 | 110 | 130 | 2.5 |
| 14 | 110 | 130 | 2.5 |
| 15 | 110 | 130 | 2.5. |

The fractions are then bulked and distilled on a 12"×1.5" Goodloe column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 65/ | 120 | 3 | 30 |
| 2 | 65 | 120 | 3 | 27 |
| 3 | 106 | 125 | 3 | 21 |
| 4 | 109 | 127 | 3 | 16 |
| 5 | 108 | 123 | 2.5 | 14 |
| 6 | 110 | 126 | 2.5 | 16 |
| 7 | 110 | 125 | 2.5 | 29 |
| 8 | 110 | 125 | 2.5 | 25 |
| 9 | 110 | 125 | 2.5 | 20 |
| 10 | 110 | 125 | 2.5 | 30 |
| 11 | 109 | 125 | 2.5 | 11 |
| 12 | 109 | 125 | 2.5 | 15 |
| 13 | 110 | 125 | 2.5 | 31 |
| 14 | 110 | 130 | 2.5 | 24 |
| 15 | 110 | 130 | 2.5 | 14. |

Bulked Fractions 7-12 of the foregoing distillation have a cardamon, figgy, date-like, vetiver, floral, rose and woody aroma with spicy, minty, fruity and rose topnotes.

FIG. 1 is the GLC profile for the crude reaction product. The peak indicated by reference numeral 10 is the peak for the mixture of compounds having the structures:

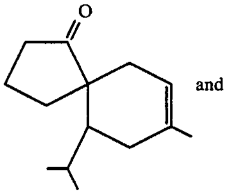
and
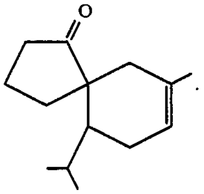
.

FIG. 2 is the NMR spectrum for peak 10 of the GLC profile of FIG. 1 for the compounds having the structures:

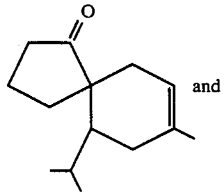
and
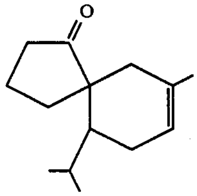

(Conditions: Field strength: 100 MHz; Solvent: $CFCl_3$).

EXAMPLE I(B)

PREPARATION OF MIXTURE OF 7 AND 8-METHYL-10-ISOPROPYL-SPIRO[4.5]DEC-7-EN-1-ONES

Reaction:

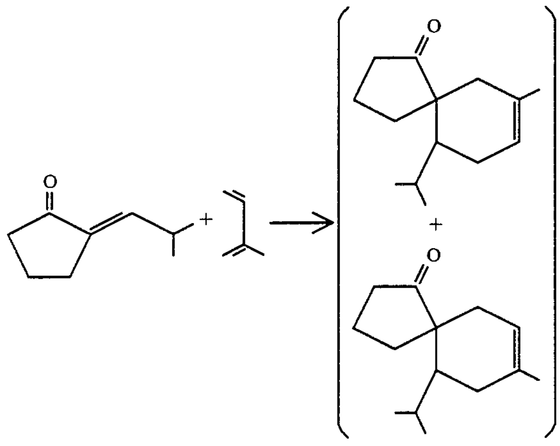

Into a 3 liter reaction flask equipped with stirrer, thermometer, reflux condenser, addition funnel, heating mantle and cooling bath is placed 800 ml methylene chloride and 160 grams of aluminum trichloride. The reaction mass is maintained at 25° C. and over a period of two hours, 690 grams of isobutyladiene cyclopentenone is added to the reaction mass (using a cooling bath). Over a period of two hours, 464 grams of isoprene is then added to the reaction mass while maintaining the reaction mass at 38°–40° C. The reaction mass is then maintained with stirring at 40° C. for a period of four hours. At the end of the four hour period, the reaction mass is quenched with 1 liter of water and then washed with 1 liter of 10% sodium carbonate. The reaction mass is then distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 20/25 | 30/67 | 100 |
| 2 | 90 | 125 | 2.0 |
| 3 | 104 | 132 | 2.0 |
| 4 | 135 | 200 | 4.0. |

FIG. 3 is the GLC profile for the crude reaction product. NMR, IR and mass spectral analyses confirm the fact that the resulting product is a mixture of compounds having the structures:

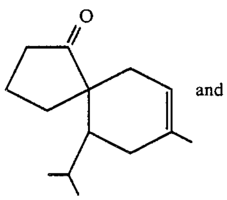
and
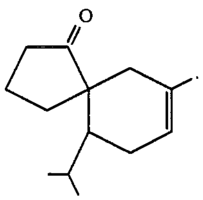

EXAMPLE II

PREPARATION OF 6 AND 9-METHYL-10-ISOPROPYL-SPIRO[4.5]DEC-7-EN-1-ONE

Reaction

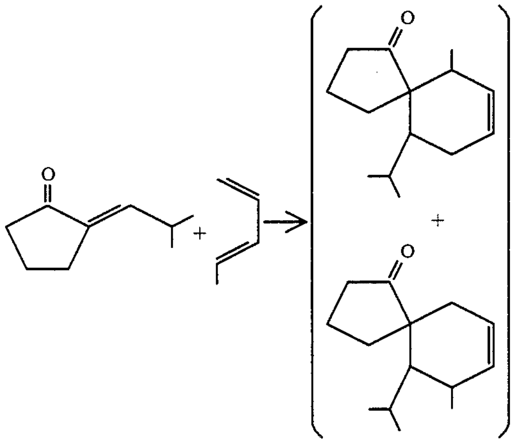

Into a 5 liter reaction flask equipped with stirrer, thermometer, reflux condenser, addition funnel, cooling bath and heating mantle is placed 600 ml methylene chloride and 80 grams of aluminum trichloride. The reaction mass is cooled to 25° C. and over a 0.5 hour period 414 grams of isobutyladiene cyclopentenone is added with stirring. The reaction mass is then heated to 40° C. and over a period of one hour 576 grams of piperylene is added to the reaction mass. The reaction mass is then heated at 40° C. for a period of 5.5 hours with stirring. At the end of the 5.5 hour period, 2 liters of water are added to the reaction mass followed by addition of 2 liters of 10% sodium carbonate. The organic mass is separated from the aqueous phase and the organic phase is then distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 80/ | 104/120 | 6.5/ |
| 2 | 67 | 125 | 5.0 |
| 3 | 82 | 125 | 4.4 |
| 4 | 100 | 126 | 4.0 |
| 5 | 104 | 126 | 3.9 |
| 6 | 104 | 130 | 3.0 |
| 7 | 105 | 133 | 3.2 |
| 8 | 105 | 160 | 3.0 |
| 9 | 106 | 205 | 2.5. |

FIG. 4 is the GLC profile for the crude reaction product.

FIG. 5 is the NMR spectrum for the compounds having the structures:

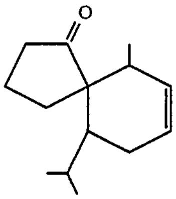 and 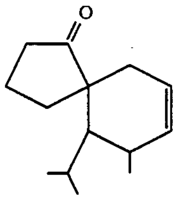

prepared according to this example.

This mixture of compounds has a rosy, woody and musky aroma with minty topnotes.

EXAMPLE III(A)

PREPARATION OF 7 AND 8-METHYL-10-ISOPROPYL-SPIRO[4.5]DEC-7-EN-1-OLS

Reaction

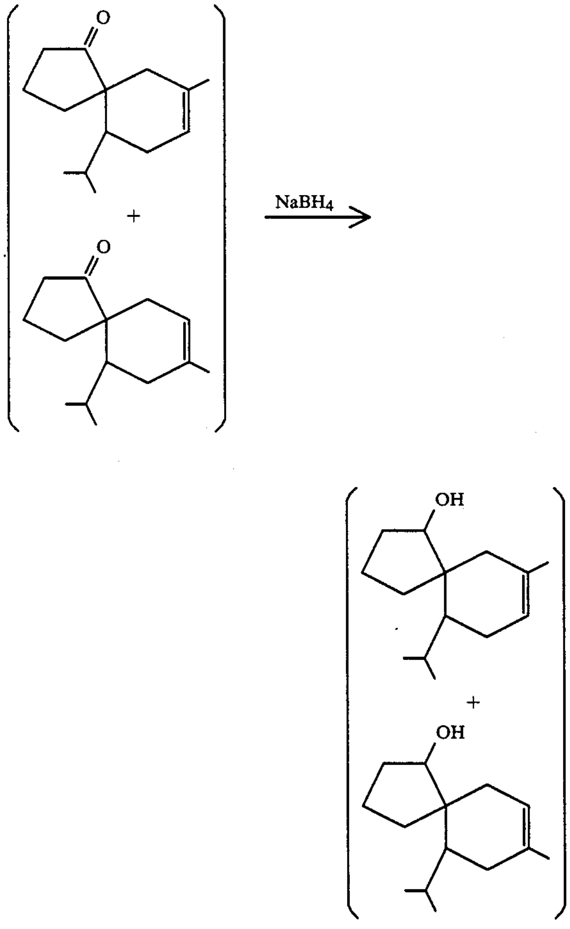

Into a 3 liter reaction flask equipped with stirrer, thermometer, reflux condenser and heating mantle is placed 400 ml of ethyl alcohol (anhydrous) and 60 grams of sodiumborohydride. The resulting mixture is heated to 60° C. and over a 0.5 hour period 400 grams of mixture of compounds having the structures:

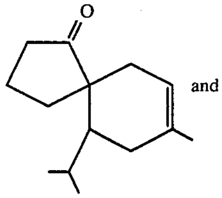 and 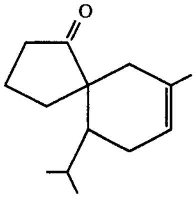

prepared according to Example I(B) is added to the reaction mass. The reaction mass is then heated to 72° C. whereupon refluxing commenced. The reaction mass is refluxed at 80° C. for a period of three hours. At the end of the three hour period, the reaction mass is admixed with 600 ml water followed by 300 ml concentrated hydrochloric acid (which is added over a 0.25 hour period). The reaction mass is cooled to room temperature and washed two times with 200 ml water. The organic phase is separated from the aqueous phase and the organic phase is distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 75/80 | 128/13 | 2.0 | 9:1 | 11 |
| 2 | 110 | 137 | 2.0 | 9:1 | 16 |
| 3 | 100 | 133 | 1.8 | 4:1 | 17 |
| 4 | 100 | 133 | 1.8 | 2:1 | 26 |
| 5 | 100 | 134 | 1.8 | 2:1 | 22 |
| 6 | 100 | 134 | 1.8 | 2:1 | 19 |
| 7 | 100 | 134 | 1.8 | 2:1 | 26 |
| 8 | 101 | 135 | 1.8 | 2:1 | 19 |
| 9 | 101 | 136 | 1.8 | 2:1 | 19 |
| 10 | 101 | 138 | 1.8 | 2:1 | 20 |
| 11 | 101 | 144 | 1.8 | 2:1 | 20 |
| 12 | 101 | 156 | 1.8 | 2:1 | 23 |
| 13 | 101 | 175 | 1.8 | 2:1 | 20 |
| 14 | 101 | 195 | 1.8 | 2:1 | 12. |

GLC, NMR, IR and mass spectral analyses confirm that the reaction mass is a mixture of compounds having the structures:

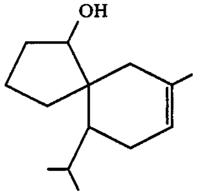 and 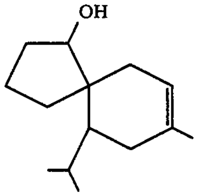.

The mixture of compounds having the structures:

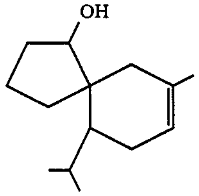 and 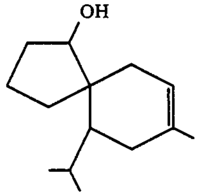

has a woody aroma with sweaty, animalic topnotes.

EXAMPLE III (B)

PREPARATION OF MIXTURE OF 7 AND 8-METHYL-10-ISOPROPYLSPIRO[4.5]DEC-7-EN-1-OL ACETATES

Reaction:

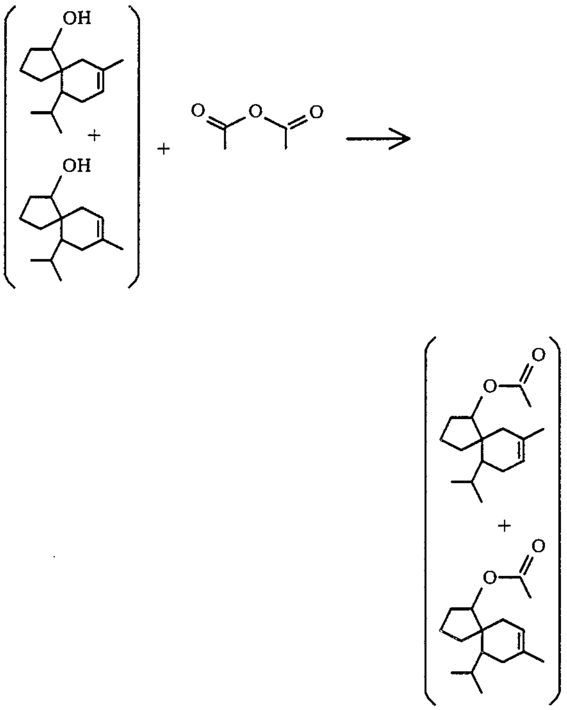

In a 250 cc reaction flask equipped with stirrer, thermometer and reflux condenser are placed 75 grams of acetic anhydride and 100 grams of the mixture of alcohols having the structures:

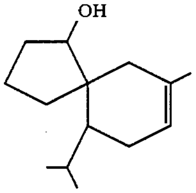
and
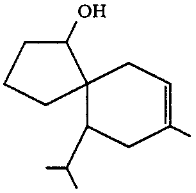

prepared according to Example III(A). The reaction mass is heated to reflux and refluxed at 125° C. for one hour. The reaction mass is then cooled to 80° C. and 200 ml water is added thereto to quench the reaction mass. The reaction mass is then washed with 200 ml water followed by 200 ml of 10% aqueous sodium bicarbonate. The organic phase is separated from the aqueous phase and the organic phase is distilled at 3 mm/Hg., 115°-128° C. The resulting product has an incense-like, olibanum aroma with sweet, woody, musky and animalic topnotes (bulked fractions 5-9 of the distillation).

FIG. 6 is the GLC profile for the crude reaction product containing the compounds having the structures:

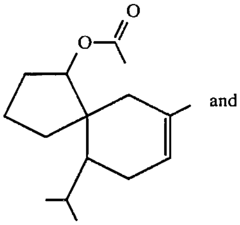
and
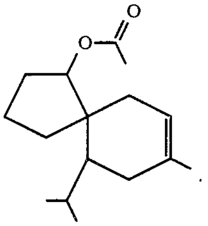

FIG. 7 is the NMR spectrum for the mixture of compounds having the structures:

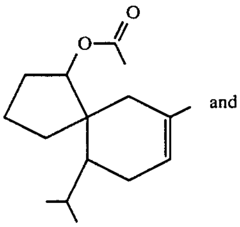
and
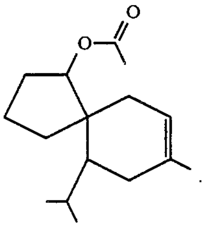

EXAMPLE IV

PREPARATION OF 7 AND 8-METHYL-10-n-BUTYL-SPIRO[4.5]DEC-7-EN-1-ONES

Reaction:

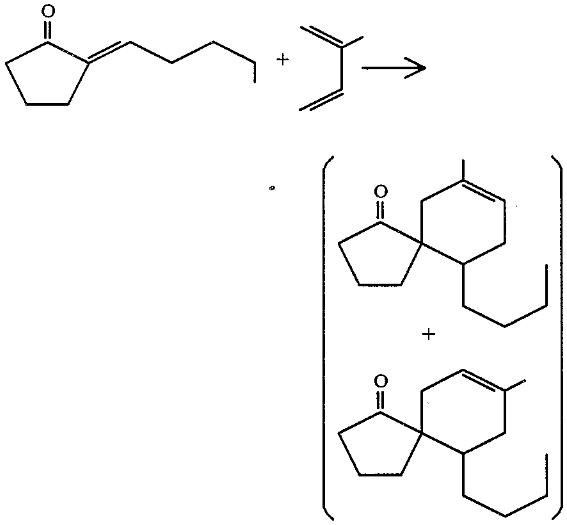

Into a 1000 ml reaction flask equipped with stirrer, thermometer, reflux condenser and cooling bath is placed 200 ml methylene dichloride and 14 grams of aluminum trichloride. Over a period of one hour while maintaining the reaction mass at 25° C., 213 grams (1.4 moles) of pentylidene cyclohexenone is added to the reaction mass. The reaction mass is then cooled to 10° C. and while maintaining the reaction mass at 10° C. with stirring over a period of two hours, 136 grams (2 moles) of isoprene is added. The reaction mass is then maintained at 10° C. for a period of five hours. The reaction mass is then fractionally distilled on a 12"×1" Goodloe column yielding the following fractions:

| Fraction No. | Vapor Temp. (°C.) | Liquid Temp. (°C.) | Vacuum mm/Hg. Pressure |
|---|---|---|---|
| 1 | 82/110 | 131/135 | 2.2/2.0 |
| 2 | 113 | 133 | 1.6 |
| 3 | 113 | 135 | 1.6 |
| 4 | 113 | 134 | 1.6 |
| 5 | | | |
| 6 | 116 | 136 | 1.6 |
| 7 | 118 | 134 | 1.6 |
| 8 | 118 | 134 | 1.6 |
| 9 | 117 | 134 | 1.6 |
| 10 | 117 | 135 | 1.6 |
| 11 | 117 | 137 | 1.6 |
| 12 | 110 | 140 | 0.8 |
| 13 | 110 | 140 | 0.8 |
| 14 | 100 | 150 | 0.6. |

The resulting product as confirmed by GLC, NMR, IR and mass spectral analyses is a mixture of compounds having the structures:

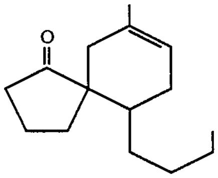
and
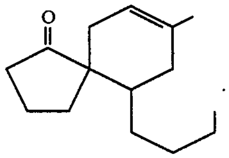
.

The mixture of compounds having the structures:

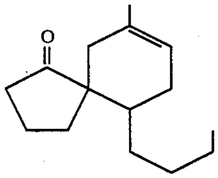
and
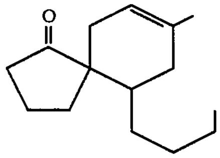

has a woody, spicy, camphoraceous, natural balsamic and lemony aroma with woody, floral, jasmine, minty and fatty topnotes.

FIG. 8 is the GLC profile for the crude reaction product containing the compounds having the structures:

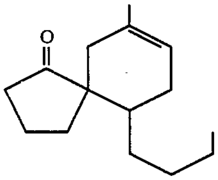
and
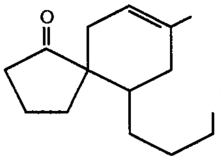
,

FIG. 9 is the NMR spectrum for Fraction 9 of the foregoing distillation containing the compounds having the structures:

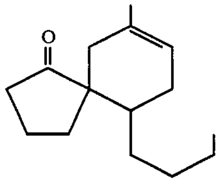
and
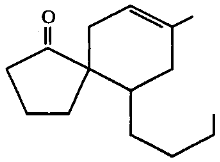

(Conditions: Field strength: 100 MHz; Solvent: $CFCl_3$).

EXAMPLE V

PERFUME FORMULATIONS

The following "woody cologne" perfume formulation is prepared:

| | Parts by Weight | | | | |
|---|---|---|---|---|---|
| Ingredients | V(A) | V(B) | V(C) | V(D) | V(E) |
| Bergamot oil | 150 | 150 | 150 | 150 | 150 |
| Orange oil | 200 | 200 | 200 | 200 | 200 |
| Lemon oil | 50 | 50 | 50 | 50 | 50 |
| Eugenol | 10 | 10 | 10 | 10 | 10 |
| 4-(4-methyl-4-hydroxy amyl) $\Delta^3$cyclohexene carboxaldehyde (LYRAL ® Trademark of International Flavors & Fragrances Inc. of New York, New York) | 40 | 40 | 40 | 40 | 40 |
| Ylang oil | 2 | 2 | 2 | 2 | 2 |
| Petitgrain Paraguay | 10 | 10 | 10 | 10 | 10 |
| γ-Methyl ionone | 20 | 20 | 20 | 20 | 20 |
| Vetiver Venezuela | 18 | 18 | 18 | 18 | 18 |
| 3-α-Methyl-dodecahydro-6,6,9a-trimethyl-naptho[2,1-b]furan | 5 | 5 | 5 | 5 | 5 |
| Product produced by the reaction of acetic anhydride, polyphosphoric acid and 1,5,9-trimethyl cyclododecatriene-1,5,9 according to the processes of Example I of U.S. Pat. No. 3,718,697, the specification for which is incorporated by reference herein | 50 | 50 | 50 | 50 | 50 |
| Octahydro-9,9-dimethyl-1,6-methano-naphthalene-1-[2H]—ol produced according to Example III of U.S. Pat. No. 3,996,169, the specification for which is incorporated by reference herein | 50 | 50 | 50 | 50 | 50 |
| Mixture of compounds having the structures: 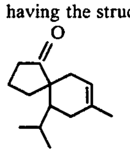 and 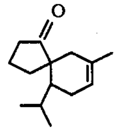 prepared according to | 12 | 0 | 0 | 0 | 0 |

-continued

| Ingredients | Parts by Weight V(A) | V(B) | V(C) | V(D) | V(E) |
|---|---|---|---|---|---|
| Example I, bulked distillation Fractions 7-12. | | | | | |
| Mixture of compounds having the structures: 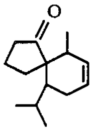 and 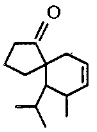 prepared according to Example II. | 0 | 12 | 0 | 0 | 0 |
| Mixture of compounds having the structures: 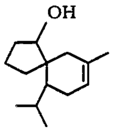 and 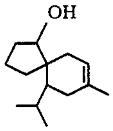 prepared according to Example III(A). | 0 | 0 | 12 | 0 | 0 |
| Mixture of compounds having the structures: 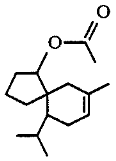 and 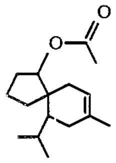 prepared according to Example III(B), bulked Fractions 5-9. | 0 | 0 | 0 | 12 | 0 |
| Mixture of compounds having the structures: 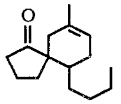 and 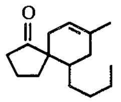 prepared according to Example IV, bulked Fractions 7-13. | 0 | 0 | 0 | 0 | 12 |

The mixture of compounds having the structures:

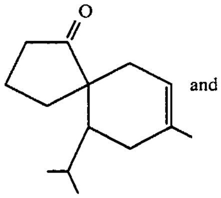 and 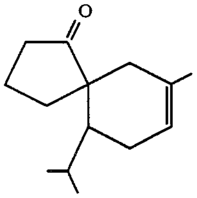

prepared according to Example I, bulked Fractions 7-12 imparts cardamon, figgy, date-like, vetiver, floral, rose and woody undertones and spicy, minty, fruity and rose topnotes to the "woody cologne" composition of Example V(A). Accordingly, the composition of Example V(A) can be described as "a woody cologne" composition with cardamon, figgy, date-like, vetiver, floral, rose and woody undertones and spicy, minty, fruity and rose topnotes.

The mixture of compounds having the structures:

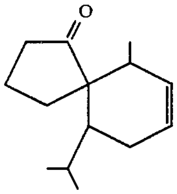 and 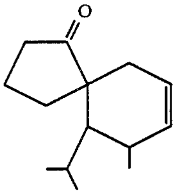

prepared according to Example II imparts rosy, woody and musky undertones and minty topnotes to the "woody cologne" composition of Example V(B). Accordingly, the composition of Example V(B) can be described as a "woody cologne" composition with rosy, woody and musky undertones and a minty topnote.

The mixture of compounds having the structures:

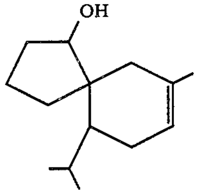 and 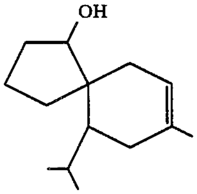

prepared according to Example III(A) imparts to the "woody cologne" composition of Example V(C), a woody undertone with sweaty and animalic topnotes. Accordingly, the composition of Example V(C) can be described as a "woody cologne" composition with woody undertones and sweaty and animalic topnotes.

The mixture of compounds having the structures:

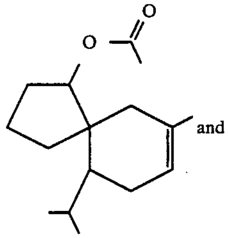
and
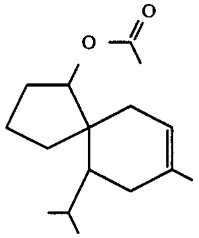

prepared according to Example III(B) (bulked distillation Fractions 5-9) imparts to the "woody cologne" composition of Example V(D) incense-like and olibanum undertones with sweet, woody, musky and animalic topnotes. Accordingly, the composition of Example V(D) can be described as a "woody cologne" composition with incense-like and olibanum undertones and sweet, woody, musky and animalic topnotes.

The mixture of compounds having the structures:

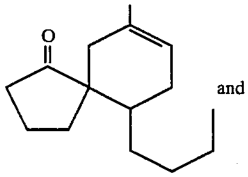
and
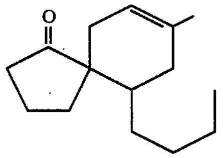

prepared according to Example IV (bulked distillation Fractions 7-3) imparts to the "woody cologne" composition of Example V(E) woody, spicy, camphoraceous, natural-balsamic and lemony undertones, with woody, floral, jasmine, minty and fatty topnotes. Accordingly, the "woody cologne" composition of Example V(E) can be described as a "woody cologne" aroma with woody, spicy, camphoraceous, natural-balsamic and lemony undertones and woody, floral, jasmine, minty and fatty topnotes.

EXAMPLE VI

PREPARATION OF COSMETIC POWDER COMPOSITION

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| Mixture of compounds prepared according to Example I having the structures: 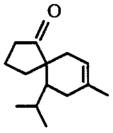 and 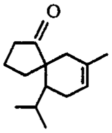 bulked distillation Fractions 7-12 | A cardamon, figgy, date-like, vetiver, floral, rose and woody aroma with spicy, minty, fruity and rosy topnotes. |
| Mixture of compounds having the structures: 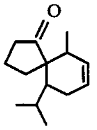 and 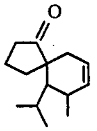 prepared according to Example II. | A rosy, woody and musky aroma with minty topnotes. |
| Mixture of compounds having the structures: 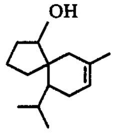 and 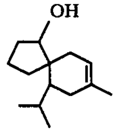 prepared according to Example III(A). | A woody aroma with sweaty and animalic topnotes. |

TABLE II-continued

| Substance | Aroma Description |
|---|---|
| Mixture of compounds having the structures: 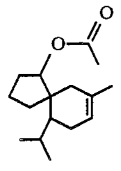 and 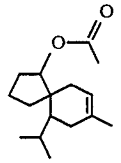 prepared according to Example III(B) (bulked distillation Fractions 5-9). | An incense-like and olibanum aroma with sweet, woody, musky and animalic topnotes. |
| Mixture of compounds having the structures: 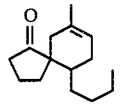 and 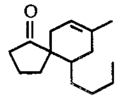 prepared according to Example IV (bulked distillation Fractions 7-13.) | A woody, spicy, camphoraceous, natural balsamic and lemony aroma with woody, floral, jasmine, minty and fatty topnotes. |
| Perfume composition of Example V(A). | A "woody cologne" composition with cardamon, figgy, date-like, vetiver, floral, rose and woody undertones and spicy, minty, fruity and rose topnotes. |
| Perfume composition of Example V(B). | A "woody cologne" composition with rosy, woody and musky undertones and a minty topnote. |
| Perfume composition of Examples V(C). | A "woody cologne" composition with woody undertones and sweaty and animalic topnotes. |
| Perfume composition of Example V(D). | A "woody cologne" composition with incense-like and olibanum undertones and sweet, woody, musky and animalic topnotes. |
| Perfume composition of Example V(E) | A "woody cologne" aroma with woody, spicy, camphoraceous, natural-balsamic and lemony undertones and woody, floral, jasmine, minty and fatty undertones. |

EXAMPLE VII

PERFUMED LIQUID DETERGENTS

Concentrated liquid detergents (Lysine salt of n-dodecylbenzene sulfonic acid as more specifically described in U.S. Pat. No. 3,948,818 issued on Apr. 6, 1976 incorporated by reference herein) with aroma nuances as set forth in Table II of Example VI, are prepared containing 0.10%, 0.15%, 0.20%, 0.25%, 0.30% and 0.35% of the substances set forth in Table II of Example VI. They are prepared by adding and homogeneously mixing the appropriate quantity of substance set forth in Table II of Example VI in the liquid detergent. The detergents all possess excellent aromas as set forth in Table II of Example VI, the intensity increasing with greater concentrations of substances as set forth in Table II of Example VI.

EXAMPLE VIII

PREPARATION OF COLOGNES AND HANDKERCHIEF PERFUMES

Compositions as set forth in Table II of Example VI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VI are imparted to the colognes and to the handkerchief perfumes at all levels indicated.

EXAMPLE IX

PREPARATION OF SOAP COMPOSITIONS

One hundred grams of soap chips [per sample] (IVORY ®, produced by the Procter & Gamble Company of Cincinnati, Ohio), are each mixed with one gram samples of substances as set forth in Table II of Example VI until homogeneous compositions are obtained. In each of the cases, the homogeneous compositions are heated under 8 atmospheres pressure at 180° C. for a period of three hours and the resulting liquids are placed into soap molds. The resulting soap cakes, in cooling, manifest aromas as set forth in Table II of Example VI.

EXAMPLE X

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| "NEODOL" ® 45-11 (a $C_{14}$-$C_{15}$ alcohol exthoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VI. Each of the detergent samples has an excellent aroma as indicated in Table II of Example VI.

EXAMPLE XI

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and their perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{20-22}$ HAPS
   22%—isopropyl alcohol;
   20%—antistatic agent
   1%—of one of the substances as set forth in Table II of Example VI.

Fabric softening compositions prepared according to Example I at column 15 of U.S. Pat. No. 3,632,396 having the aroma characteristics as set forth in Table II of Example VI, supra, consist of a substrate coating having a weight of about 3 grams per 100 square inches of substrate a first coating located directly on the substrate coating consisting of about 1.85 grams per 100 square inches of substrate; and an outer coating coated on the first coating consisting of about 1.4 grams per 100 square inches of substrate. One of the substances of Table II of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example VI, supra.

EXAMPLE XII

HAIR SPRAY FORMULATIONS

The following hair spray formulation is prepared by first dissolving PVP/VA E-735 copolymer manufactured by the GAF Corporation of 140 West 51st Street, New York, New York, in 91.62 grams of 95% of food grade ethanol. 8.0 Grams of the polymer is dissolved in the alcohol. The following ingredients are added to the PVP/VA alcoholic solution:

| Ingredient | Percent by Weight |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example VI, supra. | 0.10 |

The perfuming substances as set forth in Table II of Example VI add aroma characteristics as set forth in Table II of Example VI which are rather intense and aesthetically pleasing to the users of the soft-feel, good-hold pump hair sprays.

EXAMPLE XIII

CONDITIONING SHAMPOOS

Nonamid CMA (prepared by the Mona Industries Company) (3.0 weight percent) is melted with 2.0 weight percent coconut fatty acid (prepared by Proctor & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepen Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, New York) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example VI is added to the mixture. The resulting mixture is cooled to 40° C. and blending is carried out for an additional one hour in each case. At the end of this blending period, the resulting material has a pleasant fragrance as indicated in Table II of Example VI.

What is claimed is:

1. An alkyl-substituted spirodecenone derivative defined according to the structure:

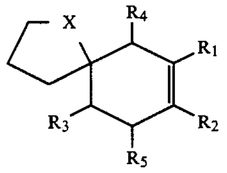

wherein X represents carbinol, carbinol $C_1$–$C_3$ alkanoate or ketone; one of $R_1$, $R_2$, $R_4$ and $R_5$ is methyl and the other of $R_1$, $R_2$, $R_4$ and $R_5$ represents hydrogen; and wherein $R_3$ represents n-butyl or isopropyl.

2. A process for augmenting or enhancing the aroma of a consumable material selected from the group consisting of perfume composition, colognes and perfumed articles comprising the step of adding to said consumable material, an aroma augmenting or enhancing quantity of the product of claim 1.

3. A mixture of compounds having the structures:

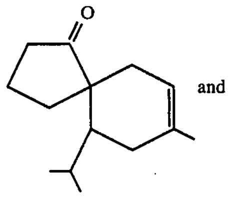

and

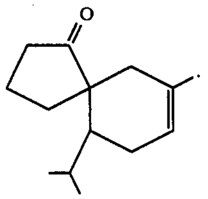

4. A mixture of compounds having the structures:

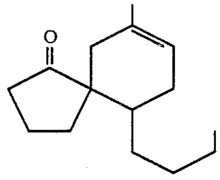 and 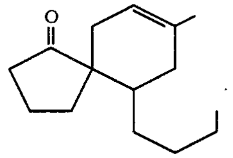.

5. A mixture of compounds having the structures:

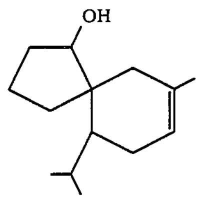 and 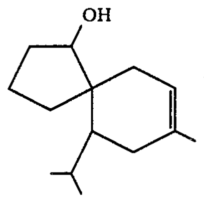.

6. A mixture of compounds having the structures:

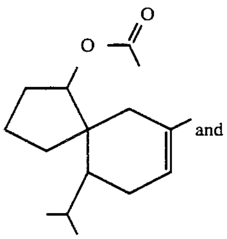 and 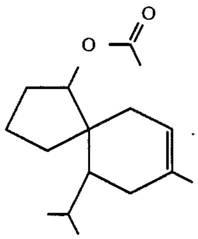.

7. A mixture of compounds having the structures:

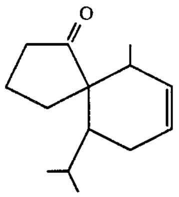 and 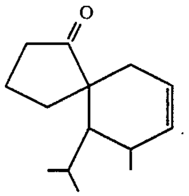.

8. A process for augmenting or enhancing the aroma of a consumable material selected from the group consisting of perfume compositions, colognes and perfumed articles comprising the step of adding to said consumable material, an aroma augmenting or enhancing quantity of the mixture of compounds of claim 3.

9. A process for augmenting or enhancing the aroma of a consumable material selected from the group consisting of perfume compositions, colognes and perfumed articles comprising the step of adding to said consumable material, an aroma augmenting or enhancing quantity of the mixture of compounds of claim 4.

10. A process for augmenting or enhancing the aroma of a consumable material selected from the group consisting of perfume compositions, colognes and perfumed articles comprising the step of adding to said consumable material, an aroma augmenting or enhancing quantity of the mixture of compounds of claim 5.

11. A process for augmenting or enhancing the aroma of a consumable material selected from the group consisting of perfume compositions, colognes and perfumed articles comprising the step of adding to said consumable material, an aroma augmenting or enhancing quantity of the mixture of compounds of claim 6.

12. A process for augmenting or enhancing the aroma of a consumable material selected from the group consisting of perfume compositions, colognes and perfumed articles comprising the step of adding to said consumable material, an aroma augmenting or enhancing quantity of the mixture of compounds of claim 7.

* * * * *